United States Patent
Petzelbauer et al.

(10) Patent No.: US 8,067,533 B2
(45) Date of Patent: Nov. 29, 2011

(54) PEPTIDES AND PEPTIDE DERIVATIVES, THE PRODUCTION THEREOF AS WELL AS THEIR USE FOR PREPARING A THERAPEUTICALLY AND/OR PREVENTIVELY ACTIVE PHARMACEUTICAL COMPOSITION

(75) Inventors: Peter Petzelbauer, Vienna (AT); Rainer Henning, Uetliburg (CH); Sonja Reingruber, Vienna (AT)

(73) Assignee: Fibrex Medical Research & Development GmbH, Vienna (AT)

( * ) Notice: Subject to any disclaimer, the term of this patent is extended or adjusted under 35 U.S.C. 154(b) by 407 days.

(21) Appl. No.: 12/280,544

(22) PCT Filed: Feb. 23, 2007

(86) PCT No.: PCT/AT2007/000096
§ 371 (c)(1),
(2), (4) Date: Sep. 30, 2008

(87) PCT Pub. No.: WO2007/095611
PCT Pub. Date: Aug. 30, 2007

(65) Prior Publication Data
US 2009/0018310 A1    Jan. 15, 2009

(30) Foreign Application Priority Data
Feb. 23, 2006    (AT) .................................. A 302/2006

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)
*A61P 17/00* (2006.01)
*A61P 29/00* (2006.01)

(52) U.S. Cl. ........................................ 530/324; 514/18.7
(58) Field of Classification Search .................. None
See application file for complete search history.

(56) References Cited

U.S. PATENT DOCUMENTS

| | | | |
|---|---|---|---|
| 4,845,075 A * | 7/1989 | Murray et al. ............... | 514/8.2 |
| 4,973,577 A * | 11/1990 | Vale et al. .................. | 514/9.9 |
| 5,637,677 A * | 6/1997 | Greene et al. ............... | 530/333 |
| 7,271,144 B2 * | 9/2007 | Petzelbauer ................. | 514/16.6 |

FOREIGN PATENT DOCUMENTS

| | | |
|---|---|---|
| WO | WO-93/21962 | 11/1993 |
| WO | WO-01/10450 | 2/2001 |
| WO | WO-02/48180 | 6/2002 |
| WO | WO-2006/000007 | 1/2006 |

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976), pp. 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Petzelbauer P. et al., "The Fibrin-Derived Peptide Bbeta15-42 Protects the Myocardium Against Ischemia-Reperfusion Injury," Nature Medicine, Nature Publishing Group, New York, NY, vol. 11, No. 3, Mar. 2005, pp. 298-304.
Zacharowski Kai et al., "A Small Molecule Derived From Fibrinogen, Bbeta15-42, Reduces Myocardial Inflammation and Injury Via Inhibition of the Adhesion Molecule VE-Cadherin," BIOSIS, 2003, Meeting Abstract.
Herrick S. et al., "Fibrinogen," International Journal of Biochemistry and Cell Biology, Exeter, GB, vol. 31, 1999, pp. 741-746.
Kamura, et al., "An Abnormal Fibrinogen Fukuoka II (Gly-Bbeta15—Cys) Characterized by Defective Fibrin Lateral Association and Mixed Disulfide Formation", Journal of Biological Chemistry, vol. 270, No. 49, Issue of Dec. 8, pp. 29392-29399, 1995.
Andreu, et al., (from Methods in Molecular Biology, v35, Peptide Synthesis Protocols Editor Rennington, et al., 1994, pp. 91-169).

* cited by examiner

*Primary Examiner* — Marcela M Cordero Garcia
(74) *Attorney, Agent, or Firm* — Maschoff Gilmore & Israelsen

(57) ABSTRACT

The invention relates to peptides and peptide derivatives of the following general Formulas (Ia) and (Ib) as well as in particular anti-inflammatory drugs containing these peptides.

(Ia)
$$H_2N\text{-}GHRPX_1X_2X_3X_4X_5X_6X_7X_8PX_9X_{10}X_{11}PX_{12}PPPX_{13}X_{14}X_{15}CGYRX_{17}$$
$$|$$
$$S$$
$$|$$
$$S$$
$$|$$
$$H_2N\text{-}GHRPX_1X_2X_3X_4X_5X_6X_7X_8PX_9X_{10}X_{11}PX_{12}PPPX_{13}X_{14}X_{15}CGYRX_{17}$$

(Ib)
$$H_2N\text{-}GHRPX_1X_2X_3X_4X_5X_6X_7X_8PX_9X_{10}X_{11}PX_{12}PPPX_{13}X_{14}CX_{15}GYRX_{17}$$
$$|$$
$$S$$
$$|$$
$$S$$
$$|$$
$$H_2N\text{-}GHRPX_1X_2X_3X_4X_5X_6X_7X_8PX_9X_{10}X_{11}PX_{12}PPPX_{13}X_{14}CX_{15}GYRX_{17}$$

6 Claims, No Drawings

PEPTIDES AND PEPTIDE DERIVATIVES, THE PRODUCTION THEREOF AS WELL AS THEIR USE FOR PREPARING A THERAPEUTICALLY AND/OR PREVENTIVELY ACTIVE PHARMACEUTICAL COMPOSITION

This application is the National Phase Under 35 U.S.C. §371 of PCT International Application No. PCT/AT2006/000096 which has an International filing date of Feb. 23, 2007, which claims priority to Austrian Application No. A302/2006 filed on Feb. 23, 2006. The entire contents of all applications listed above are hereby incorporated by reference.

The present invention relates to peptides and peptide derivatives, to the production thereof as well as to their use for preparing a therapeutically and/or preventively active drug and to such a pharmaceutical drug.

EP1586586 describes the use of peptides from the sequence of fibrin possessing anti-inflammatory effects.

Said effect may be based on the fact that the fibrin and fibrin fragments generated during the breakdown thereof bind to endothelial cells via its neo-N-terminus of the Bbeta-chain and to cells in the bloodstream via the sequence of the Aalpha-chain, thereby leading to the adhesion and transmigration of these cells into tissue. The binding partner of the fibrin and fibrin fragments to the endothelial cells is the protein vascular endothelial (VE) cadherin, which is expressed exclusively in the adherens junction between neighboring endothelial cells. The peptides according to the invention block this interaction and thereby counteract the transmigration of blood cells. The natural defense against infections by the leukocytes in the blood is not adversely affected, however. Thus, the composition of the same, such as granulocytes, lymphocytes and monocytes, remains unaffected so that the natural defense process is maintained.

Fibrinogen is produced in the liver and, in this form, is biologically inactive and normally is provided in the blood at concentrations of around 3 g/l. Proteolytic cleavage of the proenzyme prothrombin results in the formation of thrombin, which cleaves off the fibrinopeptides A and B from the fibrinogen. In this way, fibrinogen is transformed into its biologically active form. Fibrin and fibrin cleavage products are generated.

Thrombin is formed whenever blood coagulation is activated, i.e. with damage to the tissue, be it of inflammatory, traumatic or degenerative genesis. The formation of fibrin as mediated by thrombin is basically a protective process aimed at quickly sealing any defects caused to the vascular system. However, the formation of fibrin also is a pathogenic process. The appearance of a fibrin thrombus as the triggering cause of cardiac infarction is one of the most prominent problems in human medicine.

The role which fibrin plays during the extravasation of inflammatory cells from the bloodstream into the tissue, which, on the one hand, is a desired process for the defense against pathogenic microorganisms or tumor cells in the tissue, but, on the other hand, is a process which, by itself, induces or prolongs damage done to the tissue, has so far not been examined at all or not to a sufficient extent. Fibrin binds to endothelial cells via its neo-N-terminus of Bbeta by means of the sequence to Bbeta and to cells in the bloodstream by means of the sequence Aalpha, thereby leading to the adhesion and transmigration of cells into the tissue.

The peptides or proteins according to the invention may prevent the adhesion of cells from the bloodstream to endothelial cells of the vascular wall and/or their subsequent transmigration from the blood into the tissue.

WO 92/16221 describes polypeptides which are covalently linked to long-chain polymers, as for instance methoxy-polyethylene glycol (PEG). The binding of polypeptides to such polymers frequently results in a prolongation of the biological half-life of these polypeptides and delays their renal excretion. A summary of these properties may be found in Davis et al., Polymeric Materials Pharmaceuticals for Biomedical Use, pp. 441-451 (1980) The addition of PEG-groups exerts this effect in a way proportional to the molecular weight of the PEGylated peptide, as, up to a certain size of the molecule, the glomular filtration rate is inversely proportional to the molecular weight.

WO 04/101600 also describes new poly(ethylene glycol)-modified compounds and their use, in particular with emphasis on modified peptides activating the erythropoietin receptor.

Further examples for the covalent modification of peptides and proteins PEG residues are interleukins (Knauf et al., J. Biol Chem. 1988, 263, 15064; Tsutumi et al., J. Controlled Release 1995, 33, 447), Interferons (Kita et al., Drug Delivery Res. 1990, 6 157), and Catalase (Abuchowski et al., J. Biol. Chem. 1997, 252, 3582). A review of the prior art may be found in Reddy, Ann. of Pharmacotherapy, 2000, 34, 915.

A prolonged biological half-life is advantageous for various therapeutic uses of peptides. This is in particular true in cases of chronic diseases where the administration of the active agent over a prolonged period of time is indicated. With such indications this may improve the patient's compliance, as applying the active agent once a day will for instance be accepted more easily than continuous infusion. Apart from increasing the molecular mass by covalent modification, a prolongation of the persistency of polypeptides may be obtained by modifying them in such a way that their degradation by proteolytic enzymes (e.g. exo- or endoproteases or peptidases) is prevented.

Using various examples it has been shown that it is necessary to customize the appropriate modification for each peptide so as to prevent a significant influence on the pharmacodynamic effect as compared to the unmodified peptide. In this context the following may be referred to: Calcitonin (Lee et al. Pharm. Res. 1999, 16, 813), Growth Hormone Releasing Hormone (Esposito et al., Advanced Drug Delivery Reviews, 2003, 55, 1279), Glucagon like peptide 1 (Lee et al., Bioconjugate Res. 2005, 16, 377), as well as the growth hormone-receptor antagonist Pegvisomant (Ross et al., J. Clin. Endocrin. Metab. 2001, 86, 1716). The reviews by Caliceti and Veronese (Adv. Drug Deliv. Rev. 2003, 55 1261) and by Harris and Chess (Nature Rev. Drug Discovery 2003, 2, 214) discuss that in case of designing peptide- or protein-PEG-conjugates it is necessary to take into consideration the structure of the original substance, the molecular weight of the peptide and the polymer, the number of conjugated polymer chains as well as the linker chemistry, so as to obtain an effective peptide-PEG-conjugate.

Surprisingly it has now been found that peptides derived from the chain of the Bbeta(15-42)fibrin fragment, wherein one or several amino acids of the natural fibrin sequence have been substituted by other amino acids, as well as derivatives modified at the C-terminal end of the peptide sequence also have strong anti-inflammatory effects. The same applies to peptides and peptide derivatives the modification of which prevents their destruction by proteases or peptidases, as well as to peptide-PEG-conjugates derived from the basic sequence of the Bbeta(15-42)fibrin fragment.

Thus the invention relates to modified peptides which are derived from the chain of the Bbeta(1 5-42)-fibrin fragment and wherein one or several of the amino acids of the sequence have been substituted by genetically encoded or not genetically encoded amino acids or peptidomimetics. They may exist as free peptides or as C-terminal derivative and/or being linked to a polyethylene glycol (PEG)-polymer, and have anti-inflammatory and/or endothelium stabilizing effects. Esters or amides may for instance be taken into consideration as C-terminal derivatives.

The inventive compounds may have conservative substitutions of amino acids as compared to the natural sequence of fibrin of warm blooded animals in one or several positions. A conservative substitution is defined as the side chain of the respective amino acid being replaced by a side chain of similar chemical structure and polarity, the side chain being derived from a genetically coded or not genetically coded amino acid. Families of amino acids of this kind having similar side chains are known in the art. They comprise for instance amino acids having basic side chains (lysins, arginins, histidine), acidic side chains (aspartic acid, glutamic acid), uncharged polar side chains (glycine, aspartamic acid, glutamine, serine, threonine, tyrosine, cysteine), non-polar side chains (alanine, valine, leucine, isoleucine, proline, phenylalanine, methionine, tryptophan), beta-branched side chains (threonine, valine, isoleucine) and aromatic side chains (tyrosine, phenylalanine, tryptophane, histidine). Such conservative substitutions of side chains may preferably be carried out in non-essential positions. In this context, an essential position in the sequence is one wherein the side chain of the relevant amino acid is of significance for its biological effect.

The invention therefore relates to peptides and peptide derivatives of the following general formulas Ia and Ib $$\text{GHRPX}_1\text{X}_2\text{X}_3\text{X}_4\text{X}_5\text{X}_6\text{X}_7\text{X}_8\text{PX}_9\text{X}_{10}\text{X}_{11}\text{PX}_{12}\text{PPPX}_{13}\text{X}_{14}\text{X}_{15}\text{CGYRX}_{17} \text{ (SEQ ID NO: 1)} \tag{Ia}$$
$$|$$
$$S$$
$$|$$
$$S$$
$$|$$
$$\text{GHRPX}_1\text{X}_2\text{X}_3\text{X}_4\text{X}_5\text{X}_6\text{X}_7\text{X}_8\text{PX}_9\text{X}_{10}\text{X}_{11}\text{PX}_{12}\text{PPPX}_{13}\text{X}_{14}\text{X}_{15}\text{CGYRX}_{17} \text{ (SEQ ID NO: 1),}$$

$$\text{GHRPX}_1\text{X}_2\text{X}_3\text{X}_4\text{X}_5\text{X}_6\text{X}_7\text{X}_8\text{PX}_9\text{X}_{10}\text{X}_{11}\text{PX}_{12}\text{PPPX}_{13}\text{X}_{14}\text{X}_{15}\text{GCYRX}_{17} \text{ (SEQ ID NO: 2)} \tag{Ib}$$
$$|$$
$$S$$
$$|$$
$$S$$
$$|$$
$$\text{GHRPX}_1\text{X}_2\text{X}_3\text{X}_4\text{X}_5\text{X}_6\text{X}_7\text{X}_8\text{PX}_9\text{X}_{10}\text{X}_{11}\text{PX}_{12}\text{PPPX}_{13}\text{X}_{14}\text{X}_{15}\text{GCYRX}_{17} \text{ (SEQ ID NO: 2),}$$

wherein:
$X_1$-$X_{15}$ denote one of the 20 genetically coded amino acids,
$X_{17}$ denotes a residue $OR_1$, wherein $R_1$=hydrogen or ($C_1$-$C_{10}$)-alkyl),
  or a residue $NR_2R_3$, $R_2$ and $R_3$ being identical or different and denoting hydrogen or ($C_1$-$C_{10}$)-alkyl,
  or a residue -$PEG_{5-60K}$-CO—$NR_4R_5$, $R_4$ and $R_5$ being identical or different and denoting hydrogen or ($C_1$-$C_{10}$)-alkyl,
  or a residue NH—CH(CONH$_2$)—(CH$_2$)$_4$—NH—CO—Y-$PEG_{5-60K}$,
  wherein Y may in turn be an oxygen atom or an NH group,
  or a residue NH—Y—Z-$PEG_{5-60K}$, wherein Y denotes a chemical bond or a genetically coded amino acid from among the group of S, C, K or R, and Z denotes a spacer by way of which a polyethylene glycol (PEG)-residue is linked, as well as the physiologically acceptable salts thereof.

A preferred subject matter of the invention are peptides and peptide derivates of the general Formula I, wherein:
$X_1$, $X_9$, $X_{10}$, $X_{14}$ denote L, I, S, M or A,
$X_2$, $X_6$, $X_7$ denote E or D,
$X_3$, $X_4$, $X_5$, $X_{11}$ denote R or K
$X_8$, $X_{12}$ denote A, G, S, or L
$X_{13}$ denotes I, L or V
$X_{15}$ denote G, A, S or C
and wherein $X_{17}$ is as defined above,
as well as the physiologically acceptable salts thereof.

A particularly preferred subject matter of the invention are peptides and peptide derivatives of Formula IIa or IIb $$\text{GHRPLDKKREEAPSLRPAPPPISGCGYR-X}_{17} \text{ (SEQ ID NO: 3)} \tag{IIa}$$
$$|$$
$$S$$
$$|$$
$$S$$
$$|$$
$$\text{GHRPLDKKREEAPSLRPAPPPISGCGYR-X}_{17} \text{ (SEQ ID NO: 3),}$$

$$\text{GHRPLDKKREEAPSLRPAPPPISCGGYR-X}_{17} \text{ (SEQ ID NO: 4)} \tag{IIb}$$
$$|$$
$$S$$
$$|$$
$$S$$
$$|$$
$$\text{GHRPLDKKREEAPSLRPAPPPISCGGYR-X}_{17} \text{ (SEQ ID NO: 4),}$$

wherein $X_{17}$ is as defined above for Formula I, as well as the physiologically acceptable salts thereof.

A most highly preferred subject matter of the invention are compounds of Formulas (IIa) and (IIb),
wherein
$X_{17}$ denotes NH$_2$ or NR$_2$R$_3$, R$_2$ and R$_3$ being identical or different and hydrogen, or (C$_1$-C$_3$)-alkyl, or a residue -PEG$_{5-30K}$-CO—NR$_4$R$_5$, R$_4$ and R$_5$ being the same or different and hydrogen or (C$_1$-C$_3$)-alkyl,
  or a residue NH—CH(CONH$_2$)—(CH$_2$)$_4$—NH—CO—Y-PEG$_{5-30K}$, wherein Y may be an oxygen atom or an NH group
  or a residue C(NR$_2$R$_3$)—(S-succinimido)-(PEG$_{5-40K}$), the succinimide residue being linked via C-atom 3 to the sulfur atom of the cysteine residue,
as well as the physiologically acceptable salts thereof.

In the above formulas I and II the following letters represent amino acid residues in accordance with the general annotation for proteins and peptides: pPhenylalanine is F, leucine is L, isoleucine is I, methionine is M, valine is V, serine is S, proline is P, threonine is T, alanine is A, tyrosine is Y, histidine is H, glutamine is Q, asparagine is N, lysine is K, aspartic acid is D, glutamic acid is E, cysteine is C, tryptophan is W, arginine is R, glycine is G.

The amino acid residues in the compounds of Formula I may either be present in their D or their L configuration.

The term peptide refers to a polymer of these amino acids, which are linked via an amide linkage.

"Physiologically acceptable" means that salts are formed with acids or bases the addition of which does not have undesirable effects when used for humans. Preferable are salts with acids or bases the use of which is listed for use with warm blooded animals, in particular humans, in the US Pharmacopoeia or any other generally recognized pharmacopoeia.

PEG stands for a polyethylene glycol residue having a molecular weight of between 5.000 and 60.000 Dalton, this molecular weight being the maximum of a molecular weight distribution, so that individual components of the mixture may have a higher or lower molecular weight.

Subject matter of the invention furthermore is a process for the production of peptides and peptide derivatives of general Formula (I), characterized in that a monomeric peptide or peptide derivative of the general structural formulas IIIa and IIIb, $$GHRPX_1X_2X_3X_4X_5X_6X_7X_8PX_9X_{10}X_{11}PX_{12}PPPX_{13}X_{14}X_{15}CGYR—X_{17} \text{ (SEQ ID NO: 1)} \quad \text{(IIIa)}$$

$$GHRPX_1X_2X_3X_4X_5X_6X_7X_8PX_9X_{10}X_{11}PX_{12}PPPX_{13}X_{14}X_{15}GCYR—X_{17} \text{ (SEQ ID NO: 2)} \quad \text{(IIIb)}$$

is reacted to form the compounds of general structural formula (I) using a suitable oxidant. Such suitable oxidizing agents may for instance be iodine, hydrogen peroxide, organic peroxides, sodium peroxodisulfate or atmospheric oxygen with or without suitable catalysts.

The substances according to the invention and the use of the substances according to the invention for the production of a pharmaceutical drug are of particular significance for the production of a pharmaceutical drug for the therapy of diseases resulting from the tissue-damaging effect of white blood cells (leukocytes), or wherein the integrity and full physiological integrity of the layer of endothelial cells lining the blood vessels is impaired.

Diseases belonging to this group are those in context with autoimmunity, as for instance collagenoses, rheumatic diseases, inflammatory bowel diseases like Morbus Crohn or Colitis ulcerosa, psoriasis and psoriatic rheumatoid arthritis, and post/parainfectious diseases as well as diseases caused by a graft-versus-host reaction. A healing effect takes place as this medical drug blocks the migration of the leukocytes into the tissue. Thus the leukocytes remain in the blood stream and cannot cause an autoreactive effect harmful to the tissue. This effect of the inventive substances is furthermore important for the treatment of shock conditions, in particular in case of septic shock triggered by infection with gram-positive or gram-negative bacterial pathogens as well as viral infections and haemorrhagic shock caused by heavy loss of blood because of severe injuries or bacterial or viral infections.

The inventive substances may generally be used in situations that can be described with the terms "Systemic Inflammatory Response Syndrome (SIRS)", "Acute Respiratory Distress Syndrome (ARDS)" and organ- or multiorgan failure, respectively.

With a pharmaceutical drug for the therapy and/or prevention of rejection reactions of organ transplants there is a healing effect as this pharmaceutical drug prevents the migration of leukocytes from the blood stream into the donor organ, and the donor organ can therefore not be destroyed by these leukocytes and/or products formed and released by the leukocytes.

With a pharmaceutical drug for the therapy and/or prevention of arteriosclerosis there is a healing and/or preventive effect as this pharmaceutical drug blocks the migration of leukocytes into the wall of the tissue and thus the activation of the cells of the tissue wall. Thus the progress of arteriosclerosis is minimized or stopped, the progredience of arteriosclerotic plaque resulting therefrom is inhibited, causing the arteriosclerosis to recede.

With a pharmaceutical drug for the therapy and/or prevention of reperfusion trauma following surgically or pharmaceutically induced re-supply with blood, e.g. following cardiac infection, stroke, vessel surgery, cardiac bypass surgery and organ transplants, there is a healing and/or preventive effect as this pharmaceutical drug inhibits the migration of lymphocytes, neutrophils and monocytes into the wall of the vessel. Reperfusion trauma is caused by a lack of oxygen/acidosis of the cells of the vessel during its re-supply with blood, leading to their activation and/or damage. Because of this, lymphocytes, neutrophils and monocytes adhere to the vessel wall and migrate into it. Blocking the adherence and migration of lymphocytes, neutrophils and monocytes in the vessel wall causes the hypoxy/acidosis-induced damage to abate, without the subsequent inflammatory reaction causing a permanent damage to the vessel. The endothelium-stabilizing effect of the inventive compounds furthermore prevents the formation of oedemas as well as any further damage to the organs supplied via the respective blood vessels.

With a pharmaceutical drug for the therapy and/or prevention of arteriosclerosis as a consequence of metabolic diseases or the process of aging, there is a healing and/or preventive effect as this pharmaceutical drug inhibits the migration of lymphocytes and monocytes into the vessel wall, thus inhibiting the progredience of arteriosclerotic plaque resulting therefrom.

The pharmaceutical drug according to the invention may also be used for the transportation of another drug. The inventive drug specifically binds a surface molecule on endothelial cells. Thus drugs linked thereto may be delivered to endothelial cells in high concentrations without any danger of them having side effects at other sites. An example that may be cited here is the use of substances inhibiting the division of cells, which, specifically brought to endothelial cells, may have an antiangiogenetic effect. This brings about a healing effect in tumor patients, as tumor growth is blocked by preventing the proliferation of endothelial cells and thus by preventing neoangiogenesis. The inventive compounds themselves may also develop an antiangiogenetic effect, as they, because of their endothelium-stabilizing effect, prevent the endothelial cells from changing into a proliferative phenotype and thus prevent the formation of new capillary blood vessels. Therefore they are themselves suitable for the treatment of all kinds of tumor diseases as well as the prevention and/or treatment of tumor metastases.

The inventive compounds of Formula (I) together with pharmaceutical adjuvants and additives, may be formulated into pharmaceutical preparations which also are a subject matter of the present invention. In order to prepare such formulations a therapeutically effective dose of the peptide or peptide derivative is mixed with pharmaceutically acceptable diluents, stabilizers, solubilizers, emulsifying aids, adjuvants or carriers and brought into a suitable therapeutic form. Such preparations for instance contain a dilution of various buffers (e.g. Tris-HCl, acetate, phosphate) of different pH and ionic strength, detergents and solubilizers (e.g. Tween 80, Polysorbate 80), antioxidants (e.g. ascorbic acid), and fillers (e.g. lactose, mannitol). These formulations may influence the biological availability and the metabolic behavior of the active agents.

The pharmaceutical preparations according to the invention may be administered orally, parenterally (intramuscularly, intraperitoneally, intravenously or subcutaneously), transdermally or in an erodable implant of a suitable biologically degradable polymer (e.g. polylactate or polyglycolate).

The biological effect and applicability for the claimed use of the inventive compounds may for instance be determined in an assay in which a culture of human umbilical cord endothelial cells is examined microscopically after stimulation with the "N-terminal disulfide knot protein II" (NDSK-II) or with thrombin. The stimulation of endothelial cells causes the formation of gaps between the cells in a densely packed cell layer. Treatment with the inventive compounds may prevent the formation of these gaps, and is successful in closing gaps that have already been formed. This effect is predictive for the protective effect on the endothelium the inventive compounds have throughout the organism. The inventive compounds have an effect in the range of concentrations from 0.01 nM to 1 mM, preferably in the range from 1 nM to 0.1 mM in the bath solution of cells.

The effectiveness in vivo may for instance be established using a model of acute pulmonitis in a rodent. For this purpose C57 Black-mice are for instance treated as follows: the animals receive an intranasal dose of 100 ng/kg LPS, immediately after the LPS administration the mice receive the agent according to the invention (dissolved in 100 µl NaCl) i.p., a second dose is given 60 min after the administration of LPS. Control animals only receive 100 ng/kg LPS intranasally as well as saline. 6 hours after the application of LPS all groups were submitted to a bronchioalveolar lavage, and the lungs were removed. From the lavage liquids the number of neutrophils (PMN) was determined. The compounds according to the invention are effective at a dose ranging from 0.001 mg/kg body weight to 500 mg/kg body weight, preferably at a dose ranging from 0.1 mg/kg to 50 mg/kg.

A further possibility for establishing the biological effect in vivo is the reduction or complete suppression of mortality of mice because of acute peritonitis triggered by a ligature and puncture of the caecum, accompanied by septic shock. The inventive compounds bring about a reduction of this mortality at a dose ranging from 0.001 to 500 mg/kg body weight, preferably at a dose ranging from 0.1 to 50 mg/g body weight.

The following examples serve to illustrate the invention without limiting it to the examples.

General Preparation and Purification of Peptides According to the Invention

The preparation and purification of the above peptide derivatives generally takes place by way of FMOC-strategy on acid-labile resin supports using a commercially available batch peptide synthesizer as also described in the literature (e.g. "solid phase peptide synthesis—A practical approach" by E. Atherton, R. C. Sheppard, Oxford University press 1989). N-alpha-FMOC-protected derivatives, the functional side-chains of which are protected by acid-sensitive protective groups, are used as amino acid components. Unless otherwise stated, purification is carried out by means of RP-chromatography using a water/acetonitrile gradient and 0.1% TFA as ion pair reagent.

EXAMPLE 1

(Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Cys-Gly-Tyr-Arg (SEQ ID NO: 5))$_2$ Cys$^{25}$-Cys$^{25}$ Homodimeric Cystin Peptide The monomeric peptide is synthesized as in Example 1, Tentagel S—PHB-Arg(Pbf)-FMOC, (Rapp Polymer Company), at a load of 0.21 mmol/g being used as resin carrier. FMOC-Cys(Trt), (Orpegen), is used as an additional amino acid. The monomeric peptide is purified by reverse phase chromatography which gives (41 mg) of purified peptide in reduced form. Maldi-TOF 3083.6 m/z(m.i.).

The formation of the homodimer takes place by forming of an intermolecular disulfide bond. The disulfide is selectively formed by oxidation with atmospheric oxygen in slightly alkaline solution (pH 7.5-8.0) according to the dilution principle. The reaction is monitored by analyte. HPLC and mass spectrometry. The reaction is stopped by adding 0.5% TFA, and following renewed lyophilisation the RP-HPLC purification of the symmetrical homodimeric product (28 mg) takes place Maldi-TOF 6165.2 m/z (m.i.).

EXAMPLE 2

(Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Cys-Gly-Gly-Tyr-Arg (SEQ ID NO: 6))$_2$ Cys$^{24}$-Cys$^{24}$ Homodimeric Cystin Peptide The monomeric peptide is synthesized as in Example 1, Tentagel S—PHB-Arg(Pbf)-FMOC, (Rapp Polymer Company), at a load of 0.21 mmol/g being used as resin carrier. FMOC-Cys(Trt), (Orpegen), is used as an additional amino acid. The monomeric peptide is purified as in Example 1, which gives (41 mg) of purified peptide in reduced form. Maldi-TOF 3083.6 m/z(m.i.).

The formation of the homodimer takes place by formation of an intermolecular disulfide bond. For this the disulfide is selectively formed by oxidation with atmospheric oxygen in slightly alkaline solution (pH 7.5-8.0) according to the dilution principle. The reaction is monitored by analyte. HPLC and mass spectrometry. The reaction is stopped by adding 0.5% TFA, and following renewed lyophilisation the RP-HPLC purification of the symmetrical homodimeric product (28 mg) takes place Maldi-TOF 6165.2 m/z (m.i.).

EXAMPLE 3

(Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Cys-Gly-Tyr-Arg-NH$_2$ (SEQ ID NO: 7)), Cys$^{25}$-Cys$^{25}$ Homodimeric Cystin Peptide Amide 100 mg Tentagel-S-RAM (Rapp-Polymers) at a load of 0.24 mmol/g are transferred to a commercially available peptide synthesis device (PSMM (Shimadzu)), wherein the peptide sequence is constructed step-by-step according to the carbodiimide/HOBt method.

The FMOC-amino acid derivatives are pre-activated by adding a 5-fold equimolar excess of di-isopropyl-carbodiimide (DIC), di-isopropyl-ethylamine (DIPEA) und hydroxybenzotriazole (HOBt) and, following their transfer into the reaction vessel, mixed with the resin support for 30 minutes. Washing steps are carried out by 5 additions of 900 µl DMF and thorough mixing for 1 minute. Cleavage steps are carried out by the addition of 3×900 μl 30% piperidine in DMF and thorough mixing for 4 minutes.

Removal of the individual reaction and wash solutions is effected by forcing the solutions through the bottom frit of the reaction vessel.

The amino acid derivatives FMOC-Ala, FMOC-Arg(Pbf), FMOC-Asp, FMOC-Gly, FMOC-His(Trt), FMOC-Ile, FMOC-Leu, FMOC-Lys(BOC), FMOC-Pro, FMOC-Ser (tBu), FMOC-Cys(Trt) and FMOC-Tyr(tBu) (Orpegen) are employed.

FMOC-Cys(Trt), (Orpegen), is used as an additional amino acid.

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyte. RP-HPLC and mass spectrometry.

EXAMPLE 4

(Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Cys-Gly-Gly-Tyr-Arg-NH$_2$ (SEQ ID NO: 8))$_2$ Cys$^{24}$-Cys$^{24}$ Homodimeric Cystin-Peptideamide This compound is prepared as in Example 3, the sequence of peptide bond being appropriately altered.

The invention claimed is:

1. A peptide of Formula IIa or IIb

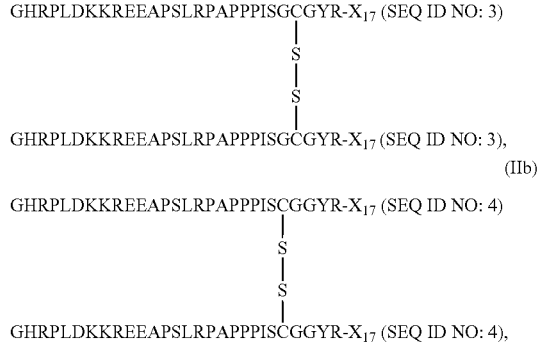

(IIa) GHRPLDKKREEAPSLRPAPPPISGCGYR-$X_{17}$ (SEQ ID NO: 3)

(IIb) GHRPLDKKREEAPSLRPAPPPISCGGYR-$X_{17}$ (SEQ ID NO: 4)

wherein $X_{17}$ denotes a residue $OR_1$, wherein $R_1$ is hydrogen or $(C_1\text{-}C_{10})$-alkyl, or a residue $NR_2R_3$, $R_2$ and $R_3$ being identical or different and denoting hydrogen or $(C_1\text{-}C_{10})$-alkyl, or a residue -$PEG_{5\text{-}60K}CONR_4R_5$, $R_4$ and $R_5$ being identical or different and denoting hydrogen or $(C_1\text{-}C_{10})$-alkyl, or a residue $NH\text{—}CH(CONH_2)\text{—}(CH_2)_4\text{—}NH\text{—}CO\text{—}Y\text{-}PEG_{5\text{-}60K}$, wherein Y may be an oxygen atom or an NH group, or a residue $NH\text{—}Y\text{—}Z\text{-}PEG_{5\text{-}60K}$, wherein Y denotes a chemical bond or a genetically coded amino acid from among the group of S, C, K or R, and Z denotes a spacer by way of which a polyethylene glycol (PEG)-residue is linked, or a physiologically acceptable salt thereof.

2. The peptide according to claim 1, wherein $X_{17}$ denotes $NH_2$, or $NR_2R_3$, $R_2$ and $R_3$ being identical or different and denoting hydrogen or $(C_1\text{-}C_3)$-alkyl, or a residue $PEG_{5\text{-}30K}CONR_4R_5$, $R_4$ and $R_5$ being the same or different and denoting hydrogen or $(C_1\text{-}C_3)$-alkyl, or a residue $NH\text{—}CH(CONH_2)\text{—}(CH_2)_4\text{—}NH\text{—}CO\text{—}Y\text{-}PEG_{5\text{-}30K}$, wherein Y denotes an oxygen atom or an NH group, or a residue $C(NR_2R_3)\text{—}(S\text{-succinimido})\text{-}(PEG_{5\text{-}40K})$, the succinimido residue being linked to the sulfur atom of the cysteine residue via C-atom 3, or a physiologically acceptable salt thereof.

3. A pharmaceutical drug composition comprising the peptide according to claim 1.

4. The peptide of claim 1, wherein $X_{17}$ denotes a residue $OR_1$, $R_1$ being hydrogen.

5. The peptide of claim 1, wherein $X_{17}$ denotes $NR_2R_3$, $R_2$ and $R_3$ being identical and denoting hydrogen.

6. The peptide of claim 1, wherein $X_{17}$ denotes a residue $OR_1$, wherein $R_1$ is hydrogen or $(C_1\text{-}C_{10})$-alkyl, or a residue $NR_2R_3$, $R_2$ and $R_3$ being identical or different and denoting hydrogen or $(C_1\text{-}C_{10})$-alkyl, or a residue -$PEG_{5\text{-}60K}CONR_4R_5$, $R_4$ and $R_5$ being identical or different and denoting hydrogen or $(C_1\text{-}C_{10})$-alkyl, or a residue $NH\text{—}CH(CONH_2)\text{—}(CH_2)_4\text{—}NH\text{—}CO\text{—}Y\text{-}PEG_{5\text{-}60K}$, wherein Y may be an oxygen atom or an NH group.

* * * * *

SEQUENCE LISTING

```
<160> NUMBER OF SEQ ID NOS: 8

<210> SEQ ID NO 1
<211> LENGTH: 29
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid
<220> FEATURE:
<221> NAME/KEY: MISC_FEATURE
```

```
<222> LOCATION: (18)..(18)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be any naturally occurring amino acid
<220> FEATURE:
<221> NAME/KEY: MOD_RES
<222> LOCATION: (25)..(25)
<223> OTHER INFORMATION: bonding site for disulfide bridge
<220> FEATURE:
<221> NAME/KEY: MISC_FEATURE
<222> LOCATION: (28)..(28)
<223> OTHER INFORMATION: when amino acid at position 29 is absent,
      amino acid at position 28 optionally modified with R1 = (C1-C10)-
      alkyl; NR2R3; -PEG5-60K-CO-NR4R5; NH-CH(CONH2)-(CH2)4-NH-CO-Y-
      PEG5-60K wherein Y denotes O or NH; or NH-Z-PEG5-60K wherein Z
      denotes a spacer
<220> FEATURE:
<221> NAME/KEY: MISC_FEATURE
<222> LOCATION: (29)..(29)
<223> OTHER INFORMATION: Xaa denotes amino acid S, C, K, R or is absent
<220> FEATURE:
<221> NAME/KEY: MOD_RES
<222> LOCATION: (29)..(29)
<223> OTHER INFORMATION: PEG5-60K linked to amino acid at position 29
      via a spacer

<400> SEQUENCE: 1

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Xaa Cys Gly Tyr Arg Xaa
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid
```

-continued

```
<220> FEATURE:
<221> NAME/KEY: MISC_FEATURE
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa can be any naturally occurring amino acid
<220> FEATURE:
<221> NAME/KEY: MOD_RES
<222> LOCATION: (24)..(24)
<223> OTHER INFORMATION: bonding site for disulfide bridge
<220> FEATURE:
<221> NAME/KEY: MISC_FEATURE
<222> LOCATION: (25)..(25)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: when amino acid at position 29 is absent,
      amino acid at position 28 optionally modified with R1 =
      (C1-C10)-alkyl; NR2R3; -PEG5-60K-CO-NR4R5; NH-CH(CONH2)-(CH2)4-
      NH-CO-Y-PEG5-60K wherein Y denotes O or NH; or NH-Z-PEG5-60K
      wherein Z denotes a spacer
<220> FEATURE:
<221> NAME/KEY: MISC_FEATURE
<222> LOCATION: (29)..(29)
<223> OTHER INFORMATION: Xaa denotes amino acid S, C, K, R or is absent
<220> FEATURE:
<221> NAME/KEY: MOD_RES
<222> LOCATION: (29)..(29)
<223> OTHER INFORMATION: PEG5-60K linked to amino acid at position 29
      via a spacer

<400> SEQUENCE: 2

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Cys Xaa Gly Tyr Arg Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MOD_RES
<222> LOCATION: (25)..(25)
<223> OTHER INFORMATION: bonding site for disulfide bridge
<220> FEATURE:
<221> NAME/KEY: MISC_FEATURE
<222> LOCATION: (28)..(28)
<223> OTHER INFORMATION: when amino acid at position 29 is absent,
      amino acid at position 28 optionally modified with R1 =
      (C1-C10)-alkyl; NR2R3; -PEG5-60K-CO-NR4R5; NH-CH(CONH2)-(CH2)4-
```

```
            NH-CO-Y-PEG5-60K wherein Y denotes O or NH; or NH-Z-PEG5-60K
            wherein Z denotes a spacer
<220> FEATURE:
<221> NAME/KEY: MISC_FEATURE
<222> LOCATION: (29)..(29)
<223> OTHER INFORMATION: Xaa denotes amino acid S, C, K, R or is absent
<220> FEATURE:
<221> NAME/KEY: MOD_RES
<222> LOCATION: (29)..(29)
<223> OTHER INFORMATION: PEG5-60K linked to amino acid at position 29
            via a spacer

<400> SEQUENCE: 3

Gly His Arg Pro Leu Asp Lys Lys Arg Glu Glu Ala Pro Ser Leu Arg
1               5                   10                  15

Pro Ala Pro Pro Pro Ile Ser Gly Cys Gly Tyr Arg Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MOD_RES
<222> LOCATION: (24)..(24)
<223> OTHER INFORMATION: bonding site for disulfide bridge
<220> FEATURE:
<221> NAME/KEY: MISC_FEATURE
<222> LOCATION: (28)..(28)
<223> OTHER INFORMATION: when amino acid at position 29 is absent,
      amino acid at position 28 optionally modified with R1 = (C1-C10)-
      alkyl; NR2R3; -PEG5-60K-CO-NR4R5; NH-CH(CONH2)-(CH2)4-NH-CO-Y-
      PEG5-60K wherein Y denotes O or NH; or NH-Z-PEG5-60K wherein Z
      denotes a spacer
<220> FEATURE:
<221> NAME/KEY: MISC_FEATURE
<222> LOCATION: (29)..(29)
<223> OTHER INFORMATION: Xaa denotes amino acid S, C, K, R or is absent
<220> FEATURE:
<221> NAME/KEY: MOD_RES
<222> LOCATION: (29)..(29)
<223> OTHER INFORMATION: PEG5-60K linked to amino acid at position 29
            via a spacer

<400> SEQUENCE: 4

Gly His Arg Pro Leu Asp Lys Lys Arg Glu Glu Ala Pro Ser Leu Arg
1               5                   10                  15

Pro Ala Pro Pro Pro Ile Ser Cys Gly Gly Tyr Arg Xaa
            20                  25

<210> SEQ ID NO 5
<211> LENGTH: 28
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MOD_RES
<222> LOCATION: (25)..(25)
<223> OTHER INFORMATION: bonding site for disulfide bridge

<400> SEQUENCE: 5

Gly His Arg Pro Leu Asp Lys Lys Arg Glu Glu Ala Pro Ser Leu Arg
1               5                   10                  15

Pro Ala Pro Pro Pro Ile Ser Gly Cys Gly Tyr Arg
            20                  25
```

```
<210> SEQ ID NO 6
<211> LENGTH: 28
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MOD_RES
<222> LOCATION: (24)..(24)
<223> OTHER INFORMATION: bonding site for disulfide bridge

<400> SEQUENCE: 6

Gly His Arg Pro Leu Asp Lys Lys Arg Glu Glu Ala Pro Ser Leu Arg
1               5                   10                  15

Pro Ala Pro Pro Pro Ile Ser Cys Gly Gly Tyr Arg
            20                  25

<210> SEQ ID NO 7
<211> LENGTH: 28
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MOD_RES
<222> LOCATION: (25)..(25)
<223> OTHER INFORMATION: bonding site for disulfide bridge
<220> FEATURE:
<221> NAME/KEY: MOD_RES
<222> LOCATION: (28)..(28)
<223> OTHER INFORMATION: AMIDATION

<400> SEQUENCE: 7

Gly His Arg Pro Leu Asp Lys Lys Arg Glu Glu Ala Pro Ser Leu Arg
1               5                   10                  15

Pro Ala Pro Pro Pro Ile Ser Gly Cys Gly Tyr Arg
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthesized peptide derivative of Bbeta
      (15-28) fibrin fragment
<220> FEATURE:
<221> NAME/KEY: MOD_RES
<222> LOCATION: (24)..(24)
<223> OTHER INFORMATION: bonding site for disulfide bridge
<220> FEATURE:
<221> NAME/KEY: MOD_RES
<222> LOCATION: (28)..(28)
<223> OTHER INFORMATION: AMIDATION

<400> SEQUENCE: 8

Gly His Arg Pro Leu Asp Lys Lys Arg Glu Glu Ala Pro Ser Leu Arg
1               5                   10                  15

Pro Ala Pro Pro Pro Ile Ser Cys Gly Gly Tyr Arg
            20                  25
```